United States Patent
Wehlus et al.

(10) Patent No.: US 10,461,276 B2
(45) Date of Patent: Oct. 29, 2019

(54) ORGANIC OPTOELECTRONIC COMPONENT AND METHOD OF PREVENTING THE ANALYSIS OF THE MATERIAL COMPOSITION OF AN ORGANIC OPTOELECTRONIC COMPONENT

(71) Applicant: OSRAM OLED GmbH, Regensburg (DE)

(72) Inventors: Thomas Wehlus, Lappersdorf (DE); Daniel Riedel, München (DE); Arne Fleißner, Regensburg (DE); Armin Heinrichsdobler, Regensburg (DE); Nina Riegel, Tegernheim (DE)

(73) Assignee: OSRAM OLED GmbH, Regensburg (DE)

( * ) Notice: Subject to any disclaimer, the term of this patent is extended or adjusted under 35 U.S.C. 154(b) by 0 days.

(21) Appl. No.: 15/770,432

(22) PCT Filed: Feb. 14, 2017

(86) PCT No.: PCT/EP2017/053275
§ 371 (c)(1),
(2) Date: Apr. 23, 2018

(87) PCT Pub. No.: WO2017/148697
PCT Pub. Date: Sep. 8, 2017

(65) Prior Publication Data
US 2018/0358575 A1    Dec. 13, 2018

(30) Foreign Application Priority Data
Mar. 3, 2016 (DE) .......... 10 2016 103 821

(51) Int. Cl.
*H01L 51/52* (2006.01)
*G01N 21/3563* (2014.01)
(Continued)

(52) U.S. Cl.
CPC ..... *H01L 51/5253* (2013.01); *G01N 21/3563* (2013.01); *G01N 21/65* (2013.01); *G01N 23/20091* (2013.01)

(58) Field of Classification Search
CPC ............ H01L 51/5253; G01N 21/3563; G01N 23/20091
See application file for complete search history.

(56) References Cited

U.S. PATENT DOCUMENTS 8,963,413 B2* 2/2015 Fischer ............. B32B 17/10073
313/504
9,092,706 B2* 7/2015 Seo .................. G06K 19/06046
(Continued)

FOREIGN PATENT DOCUMENTS

| DE | 102 52 787 A1 | 11/2003 |
|---|---|---|
| DE | 10 2013 106 508 A1 | 12/2014 |
| DE | 10 2013 106 855 A1 | 1/2015 |
| EP | 1 634 697 A1 | 3/2006 |

OTHER PUBLICATIONS

Kindermann, M., "Characteristic groups and their oscillations in IR spectroscopy for practical instrumental analysis for biochemists", *Test Infrared Spectroscopy*, University of Greifswald—Institute of Biochemistry, http://www.mnf.unigreifswald.de/fileadmin/Biochemie/grundpraktika/isa_biochemiker/Gruppenfrequenzen.pdf.

*Primary Examiner* — Dominic J Bologna
(74) *Attorney, Agent, or Firm* — DLA Piper LLP (US)

(57) ABSTRACT

A method of preventing an analysis of the material composition of an organic optoelectronic component includes: A) providing an organic optoelectronic component having a functional component part and a camouflage layer, and B) determining an overall analysis spectrum of the organic optoelectronic component by IR or X-ray radiation, wherein the overall analysis spectrum is composed of a first analysis spectrum of the functional component part and a second analysis spectrum of the camouflage layer, and determina-
(Continued)

tion of the first and/or second analysis spectrum from the overall analysis spectrum is made more difficult or prevented so that, due to the camouflage layer, determination of the material composition of the functional component part is made difficult or prevented.

17 Claims, 3 Drawing Sheets

(51) Int. Cl.
*G01N 21/65* (2006.01)
*G01N 23/20091* (2018.01)

(56) References Cited

U.S. PATENT DOCUMENTS

| | | | |
|---|---|---|---|
| 2006/0062995 A1* | 3/2006 | Yamamoto | B32B 27/08 |
| | | | 428/332 |
| 2007/0164666 A1* | 7/2007 | Oosono | H01L 51/524 |
| | | | 313/504 |
| 2011/0278547 A1* | 11/2011 | Utsumi | H01L 51/5253 |
| | | | 257/40 |
| 2012/0080615 A1* | 4/2012 | Kingsley | C09K 11/025 |
| | | | 250/459.1 |
| 2016/0149153 A1 | 5/2016 | Scharner et al. | |
| 2016/0372700 A1 | 12/2016 | Baisl et al. | |
| 2019/0109299 A1* | 4/2019 | Riedel | H01L 51/5268 |

* cited by examiner

ORGANIC OPTOELECTRONIC COMPONENT AND METHOD OF PREVENTING THE ANALYSIS OF THE MATERIAL COMPOSITION OF AN ORGANIC OPTOELECTRONIC COMPONENT

TECHNICAL FIELD

This disclosure relates to an organic optoelectronic component and a method of preventing the analysis of the material composition of an organic optoelectronic component.

BACKGROUND

Organic optoelectronic components, for example, organic light-emitting diodes can be used in the automobile sector. A stable encapsulation is necessary for this purpose. The encapsulation can have a multiplicity of thin layers, which are layered one on top of the other and form a hermetically sealed encapsulation layer. For example, this encapsulation layer can be a thin-film encapsulation layer (TFE). Knowledge about the structure and the layer sequence of such an encapsulation is generally an essential secret of the respective manufacturers. The organic optoelectronic components can be analyzed and thus copied (reverse engineering). A counterfeit of organic optoelectronic components and the sale thereof, for example, under false brand names can also pose a problem.

It could therefore be helpful to provide an organic optoelectronic component that is secure. In particular, it could be helpful to provide an organic optoelectronic component that is copy-protected and/or easily identifiable, that is to say it can easily be assigned to a specific manufacturer. The copy protection should in particular be easy to detect.

SUMMARY

We provide a method of preventing an analysis of the material composition of an organic optoelectronic component including:
A) Providing an organic optoelectronic component having a functional component part and a camouflage layer, and
B) Determining an overall analysis spectrum of the organic optoelectronic component by IR or X-ray radiation,
wherein the overall analysis spectrum is composed of a first analysis spectrum of the functional component part and a second analysis spectrum of the camouflage layer, and
determination of the first and/or second analysis spectrum from the overall analysis spectrum is made more difficult or prevented so that, due to the camouflage layer, determination of the material composition of the functional component part is made difficult or prevented.

We also provide an organic optoelectronic component including a functional component part and a camouflage layer, wherein the functional component part includes a substrate, a first electrode on the substrate, an organic functional layer stack on the first electrode, a second electrode arranged at least in regions on the organic functional layer stack, and an encapsulation on the second electrode, wherein the functional component part emits electromagnetic radiation and has a first analysis spectrum, the camouflage layer has a second analysis spectrum, the first analysis spectrum and the second analysis spectrum are different from one another, overlap at least in some regions, and form an overall analysis spectrum of the organic optoelectronic component such that, due to the camouflage layer, an analysis of the material composition of the functional component part is made difficult or prevented.

LIST OF REFERENCE NUMERALS 100 organic optoelectronic component
10 functional component part
11 substrate
12 first electrode
13 organic functional layer stack
14 second electrode
15 encapsulation
151 protective layer
152 adhesive layer
16 first analysis spectrum
17 EDX bulb
20 camouflage layer
26 second analysis spectrum
30 further camouflage layer
G total analysis spectrum
x main beam direction

DETAILED DESCRIPTION

Our organic optoelectronic component has a functional component part and a camouflage layer. The functional component part has a substrate, a first electrode on the substrate, an organic functional layer stack on the first electrode, a second electrode on the organic functional layer stack arranged at least in regions on the organic functional layer stack, and an encapsulation on the second electrode. The functional component part emits electromagnetic radiation. The functional component part has a first analysis spectrum. The camouflage layer has a second analysis spectrum. In particular, the first analysis spectrum and the second analysis spectrum are different from one another. The first analysis spectrum and the second analysis spectrum overlap at least in regions and form an overall analysis spectrum of the organic optoelectronic component. As a result, due to the camouflage layer, an analysis of the material composition of the functional component part is made more difficult or prevented.

A layer or an element arranged or applied "on" or "over" another layer or another element means that the one layer or the one element is arranged directly, i.e. in direct mechanical and/or electrical contact, on the other layer or the other element. Furthermore, it can also mean that the one layer or the one element is arranged indirectly on or above the other layer or the other element. In this case, further layers and/or elements can then be arranged between the one and the other layer or between the one and the other element.

The organic optoelectronic component may have a functional component part. In this context, functional means that the component part emits electromagnetic radiation during operation. In particular, the functional component part emits electromagnetic radiation from the visible region, in particular at wavelengths of 400 nm to 800 nm, for example, 450 nm to 550 nm. In other words, the camouflage layer is not required to emit radiation. In particular, the camouflage layer is not capable of emitting electromagnetic radiation.

The functional component part may have a substrate. The substrate can comprise, for example, one or more materials in the form of a layer, a plate, a film or a laminate selected from glass, quartz, plastic, metal and silicon wafer. In particular, the substrate comprises glass or consists thereof.

The functional component part may have at least two electrodes, a first and a second electrode. In particular, the organic functional layer stack is arranged between the two electrodes. In particular, the first electrode faces the substrate and the second electrode faces away from the substrate.

At least one of the electrodes may be transparent. The term 'transparent layer' denotes a layer transmissive to visible light. In this case, the transparent layer can be clearly translucent or at least partially light-diffusing and/or partially light-absorbing so that the transparent layer can, for example, also be diffusely or milkily translucent. Particularly preferably, a layer referred to here as transparent is as light-transmissive as possible so that in particular absorption of light or radiation generated during operation of the component in the functional layer stack is as low as possible.

Both electrodes may be transparent. Light generated in the organic functional layer stack can thus be radiated in both directions, i.e. through both electrodes. In the event that the organic optoelectronic component has a substrate, this means that light passes through the substrate, which is then likewise transparent, and can be radiated into the direction facing away from the substrate. Furthermore, in this case, all layers of the organic optoelectronic component can be transparent so that the organic optoelectronic component forms a transparent OLED. Furthermore, it can also be possible that one of the two electrodes between which the functional layer stack is arranged is not transparent and preferably reflective. Light generated in the at least one organic functional layer stack can thus be emitted only in one direction through the transparent electrode. In particular, this direction is the main beam direction or main direction x. If the electrode arranged on the substrate and the substrate are transparent, this is also referred to as a bottom emitter, while when the electrode arranged facing away from the substrate is transparent, this is referred to as a top emitter.

A transparent electrically conductive oxide, for example, can be used as the material for a transparent electrode. Transparent, electrically conductive oxides ("TCOs" for short) are transparent, electrically conductive materials, generally metal oxides such as, for example, zinc oxide, tin oxide, cadmium oxide, titanium oxide, indium oxide or indium tin oxide (ITO). In addition to binary metal-oxygen compounds such as, for example, $ZnO$, $SnO_2$ or $In_2O_3$, ternary metal-oxygen compounds such as, for example, $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides belong to the group of TCOs. Furthermore, it is possible that the TCOs do not necessarily correspond to a stoichiometric composition and can also be p-doped or n-doped. In particular, the first electrode is designed as an anode and has a transparent electrically conductive oxide.

The second electrode may be designed as a cathode. The cathode material can be advantageously, inter alia, in particular aluminium, barium, indium, silver, gold, magnesium, calcium, copper, yttrium, terbium, samarium or lithium as well as compounds, combinations and alloys thereof.

The functional component part may have an organic functional layer stack. The organic functional layer stack is arranged on the first electrode. The organic functional layer stack has at least one active layer or a plurality thereof. The active layer of an organic optoelectronic component or the plurality thereof can contain organic polymers, organic oligomers, organic monomers, organic small non-polymeric molecules ("small molecules") or combinations thereof. Furthermore, the active layer can be in the form of an electron-luminescent layer. Materials having a radiation emission on the basis of fluorescence or phosphorescence are suitable as materials for this purpose, for example, polyfluorene, polythiophene or polyphenylene or derivatives, compounds, mixtures or copolymers thereof.

The organic functional layer stack can comprise further functional layers such as, for example, electroluminescent layers, hole-injection layers, hole-blocking layers, electron-transport layers, electron-blocking layers and/or electron-injection layers.

The organic optoelectronic component may be formed as an organic light-emitting diode (OLED).

The functional component part may have an encapsulation. Encapsulation means a device set up to form a barrier to atmospheric substances, in particular to moisture and oxygen. In other words, the encapsulation is designed such that it can be penetrated to only a very small extent by atmospheric substances such as water or oxygen, and/or air and humidity diffusion are clearly retarded relative to previous encapsulations.

The encapsulation is preferably a thin-film encapsulation. The encapsulation can have one or more thin layers deposited, for example, by chemical vapor deposition (CVD) or PECVD ("plasma enhanced chemical vapor deposition") and/or an atomic layer deposition method (ALD) and, for example, contain one or more materials from the group of silicon oxide, silicon carbide, silicon nitride, aluminum oxide, tin oxide, zirconium oxide, titanium oxide, hafnium oxide, lanthanum oxide and tantalum oxide. The encapsulation can furthermore, for example, have a mechanical protection in the form of a plastic layer and/or a laminated glass layer and/or laminated metal foil, for example, made of aluminium, on a thin-film encapsulation. In this way, for example, a scratch protection can be achieved.

Alternatively, other encapsulations are also possible, for example, in the form of a glued-on glass cover. In particular, the glass lid or the glass is arranged on a thin-film encapsulation by an adhesive or an adhesive layer.

The functional component part may have a first analysis spectrum. The analysis spectrum is understood as the analysis result obtained when the functional component part or the camouflage layer is produced by physical methods in which a radiation is decomposed according to a certain property such as energy, wavelength, mass and the like. The analysis spectrum can be part of the material analysis to determine the material composition of the corresponding components, in particular in the functional component part. For example, the first and/or second analysis spectrum can be an absorption spectrum, an emission spectrum and/or a frequency spectrum.

The organic optoelectronic component may have a camouflage layer. The camouflage layer has, in particular, a second analysis spectrum. A layer or a plurality of layers is referred to as a camouflage layer introduced into the organic optoelectronic component and impedes or prevents the material analysis of the functional component part. The camouflage layer can be a copy protection. The camouflage layer can alternatively or additionally identify the component of a specific manufacturer. In particular, the camouflage layer is designed to emit no radiation, in particular electromagnetic radiation from the visible region. In particular, the camouflage layer does not influence the electro-optical behavior and/or the radiation emission of the functional component part and/or the functionality of the organic optoelectronic component, or, if it does, only insignificantly.

The first and/or second analysis spectrum may be an IR and/or Raman spectrum. In other words, at least the functional component part and/or the camouflage layer have/has been examined by infrared spectroscopy and, for example, the intensity is registered as a first and/or second analysis spectrum as a function of the wavelength.

The Raman spectrum means the intensity wavelength spectrum by elastic scattering of light on molecules or solids (Raman scattering).

The first and/or second analysis spectrum may each be an EDX spectrum. EDX stands for energy-dispersive x-ray spectroscopy. This is a measurement method of material analysis associated with X-ray spectroscopy. In other words, atoms in the materials of the functional component part or of the camouflage layer are excited by an electron beam of uniform energy, the materials then emit X-rays for the respective element of specific energy, which can in turn be graphically represented in an EDX spectrum.

The first and/or second analysis spectrum may each be an elementary analysis spectrum.

The first analysis spectrum and the second analysis spectrum may be different from one another. In other words, the camouflage layer and the functional component part have different materials or at least partially different materials, which in turn have different analysis spectra, in particular a first and a second analysis spectrum. The first and second analysis spectra overlap at least in regions and form an overall analysis spectrum of the organic optoelectronic component. In particular, the first and the second analysis spectrum are additively superimposed.

We found that, by introducing a camouflage layer into an organic optoelectronic component, an analysis of the functional component part is made more difficult or prevented. The camouflage layer thus forms an easily detectable copy protection. In particular, the camouflage layer can be easily detected analytically. On the basis of the difficult backward analysis, that is to say the determination of the first and/or second analysis spectrum from the overall analysis spectrum, in addition, a concealment of the used materials and layers present in the functional component can be effected, and thus a forgery-proof component is provided. This can be achieved in particular by superimposition of the material signals of the organic functional layer stack, the encapsulation, the electrodes and the camouflage layer. For example, it is possible to fake the material for the adhesive layer or, for example, for the lamination of the protective layer, which is made of aluminium or glass, for example.

The camouflage layer can be applied by structured processing methods such as screen printing or ink jet printing. Thus, in particular, only the encapsulation can be covered with the camouflage layer and the electrodes can be free of the camouflage layer.

The camouflage layer can promote homogenization of the temperature of the organic optoelectronic component depending on the material.

The camouflage layer may be arranged between the second electrode and the encapsulation. In particular, the camouflage layer is arranged in direct contact with both the second electrode and the encapsulation.

That one layer or one element is arranged "between" two other layers or elements can mean that the one layer or the one element is arranged directly at, i.e. in direct mechanical and/or electrical contact, or in indirect contact with, one of the two other layers or elements and in direct mechanical and/or electrical contact or in indirect contact with the other of the two other layers or elements. In indirect contact, further layers and/or elements can be arranged between the one and at least one of the two other layers or between the one and at least one of the two other elements.

The camouflage layer may be arranged between the substrate and the first electrode. In particular, the camouflage layer is arranged in direct contact with both the substrate and the first electrode.

The camouflage layer may be arranged outside the beam path of the electromagnetic radiation, in particular outside the main beam direction x, of the functional component part.

The camouflage layer may have a layer thickness of 1 nm or 20 nm to 5000 nm, in particular 1 nm to 1000 nm, particularly preferably 20 nm to 500 nm.

The encapsulation may have a layer structure. The layer structure comprises at least one protective layer and one adhesive layer. In particular, the adhesive layer is arranged between the protective layer and the organic functional layer stack. In particular, the camouflage layer is arranged between the protective layer and the adhesive layer.

The organic optoelectronic component may have a further camouflage layer. The further camouflage layer can have the definitions and structures as already mentioned above for the camouflage layer. In particular, the further camouflage layer has a different material composition compared to the camouflage layer. The further camouflage layer can be arranged between the organic functional layer stack and the adhesive layer, in particular in direct mechanical contact with both the organic functional layer stack and the adhesive layer. The encapsulation then has two camouflage layers that impede or prevent a material analysis of the functional component part.

The encapsulation may have a layer structure comprising a protective layer and an adhesive layer, wherein the adhesive layer forms the camouflage layer. In particular, the adhesive layer has IR-active materials that make an analysis of the material composition of the functional component part difficult or prevent the same.

The camouflage layer may have materials not present in the functional component part. In other words, the camouflage layer can have a different analysis spectrum compared to the functional component part and thus cause a fake of the material composition of the functional component part.

The camouflage layer may be formed as an adhesive layer of the encapsulation. In particular, the camouflage layer is arranged in direct contact with the organic functional layer stack and the protective layer of the encapsulation. As a result, a possible analysis is made difficult due to mechanical separation.

The camouflage layer may comprise an inorganic material or an oxide of an inorganic material. In particular, the inorganic material is selected from a group consisting of silicon, indium, aluminium, gold, copper, platinum, titanium, iridium, tin and zinc.

In particular, the inorganic materials can be determined by X-ray spectroscopy or elementary analysis.

The camouflage layer may comprise or consist of an organic polymeric material. In particular, the organic polymeric material is selected from the group consisting of infrared and/or Raman-active materials. In particular, the organic polymeric material is selected from:
alcohols, phenols
amines
carboxylic acids
aromatics, oliphines
saturated hydrocarbons
thiols, thiophenols
acetylenes, nitriles isocyanates, isothiocyanates, nitriles
carbonyl compounds
oliphins
aromatics
nitro compounds
sulfonyl compounds
amides
nitro compounds
ethers, esters, anhydrides, acetals
solfoxides
oliphins
halogen compounds
thioether.

The camouflage layer may comprise an organic polymeric material selected from the group consisting of polyimide, poly (p-phenylene) (PPP), poly (p-phenylene-vinylene) (PPV), acrylate, epoxide, silicone and polyurethane.

Our method prevents the analysis of the material composition of an organic optoelectronic component. The same definitions and structures as mentioned above for the organic optoelectronic component are preferably specified.

The method may comprise the following method steps:

A) Provision of an organic optoelectronic component having a functional component part and a camouflage layer, B) Determination of an overall analysis spectrum of the organic optoelectronic component by IR or X-ray radiation, wherein the overall analysis spectrum is composed of a first analysis spectrum of the functional component part and a second analysis spectrum of the camouflage layer, wherein the determination of the first and/or second analysis spectrum from the overall analysis spectrum is made more difficult or prevented so that, due to the camouflage layer, the determination of the material composition of the functional component part is made more difficult, in particular prevented.

We found that, as a result of the presence of a camouflage layer in an organic optoelectronic component, identification of the material composition of the functional component part is made more difficult or prevented and competitive advantages can thus be ensured.

Further advantages, advantageous structures and developments will become apparent from the examples described below in conjunction with the figures.

In the examples and figures, identical or identically acting elements can each be provided with the same reference symbols. The elements illustrated and their size relationships among one another are not to be regarded as true to scale. Rather, individual elements such as, for example, layers, components and regions are represented with an exaggerated size for better representability and/or for a better understanding.

Figure 1:
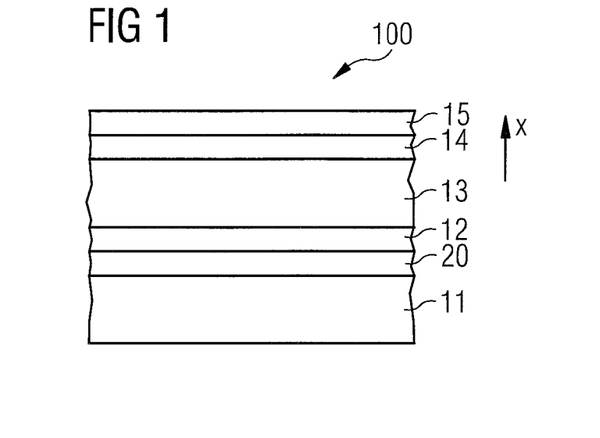
FIGS. 1 to 6 each show a schematic side view of an organic optoelectronic component according to an example.

FIG. 1 shows a schematic side view of an organic optoelectronic component 100 according to an example. The component 100 has a substrate 11, for example, made of glass. A camouflage layer 20 is arranged directly downstream of the substrate 11. The camouflage layer 20 can have an IR-active and/or Raman-active and/or X-ray-active material, for example, Si. The camouflage layer 20 has a second analysis spectrum that can be composed of the spectral signals of the materials of the camouflage layer 20. A first electrode 12 is arranged downstream of the camouflage layer 20. The first electrode 12 is followed directly by an organic functional layer stack 13 and, in turn, a second electrode 14. The organic optoelectronic component 100 can have an encapsulation 15, in particular a thin-film encapsulation.

Figure 2:
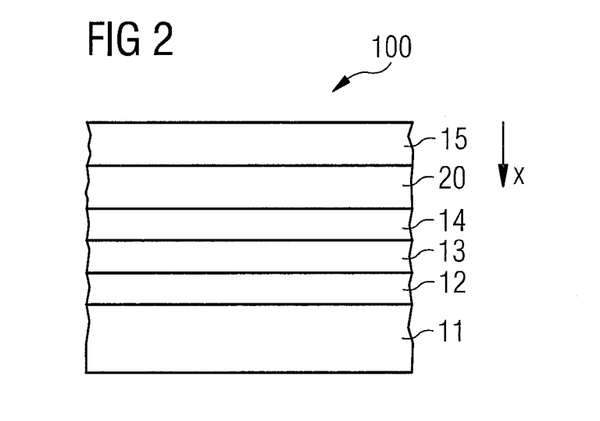

FIG. 2 shows a schematic side view of an organic optoelectronic component 100 according to an example. The organic optoelectronic component 100 of FIG. 2 differs from the component of FIG. 1 in that the camouflage layer 20 is arranged between the second electrode 14 and the encapsulation 15. Furthermore, both components of FIGS. 1 and 2 differ in their configuration as bottom emitter (FIG. 2) and top emitter (FIG. 1) according to the main beam direction x.

Figure 3:
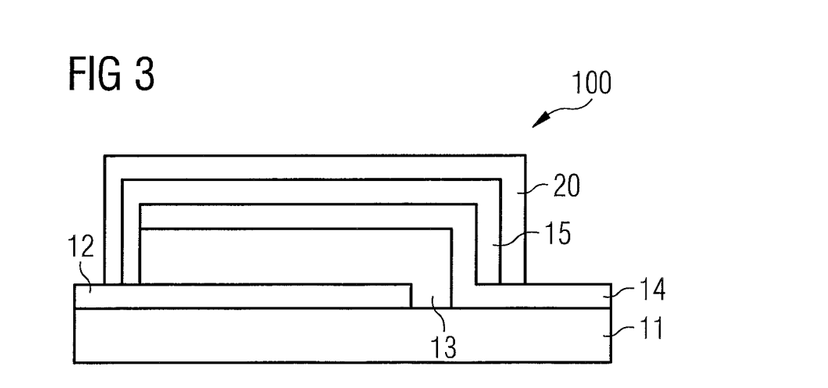

FIG. 3 shows a schematic side view of an organic optoelectronic component 100 according to an example. The component 100 has a substrate 11. A first electrode 12, an organic functional layer stack 13 and a second electrode 14 are arranged downstream of the substrate 11. The component 100 has an encapsulation 15 and a camouflage layer 20 that surrounds the encapsulation 15 in a material- and form-fitting manner. The camouflage layer 20 can fulfil two functions. On the one hand, it can output a typical EDX or IR signal as a copy protection. On the other hand, it can prevent the detection and clear assignment of the materials to the underlying layers of the component 100.

Figure 4:
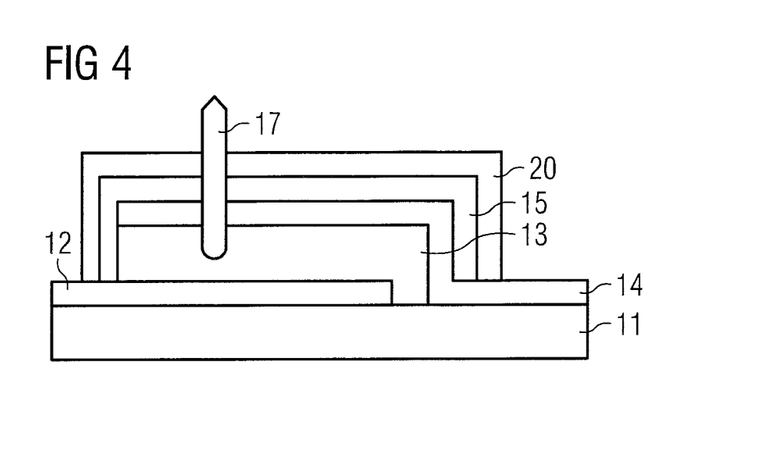

FIG. 4 shows a schematic side view of an organic optoelectronic component 100 according to an example. The component 100 of FIG. 3 differs from the component 100 of FIG. 4 in that the component of FIG. 4 additionally has a so-called ionization bulb, in particular an EDX ionization bulb 17. The term 'ionization bulb' is known in the art with regard to X-ray spectroscopy and is therefore not explained in more detail.

Figure 5:
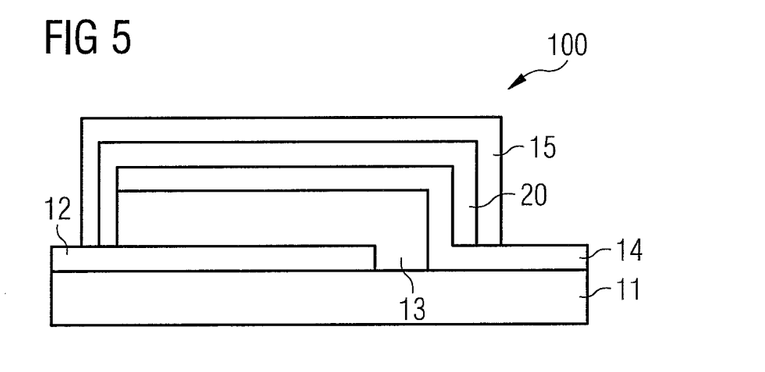

FIG. 5 shows a schematic side view of an organic optoelectronic component 100 according to an example. The component 100 of FIG. 5 differs from the component 100 of FIG. 3 in that the camouflage layer 20 and the encapsulation 15 are interchanged. In other words, the camouflage layer 20 is arranged directly downstream of the second electrode 14. The camouflage layer 20 is arranged directly downstream of the encapsulation 15. The camouflage layer can generate a well-defined element signal, for example, by EDX or IR, which can lead to a camouflage of the material analysis of the functional component part 10.

Figure 6:
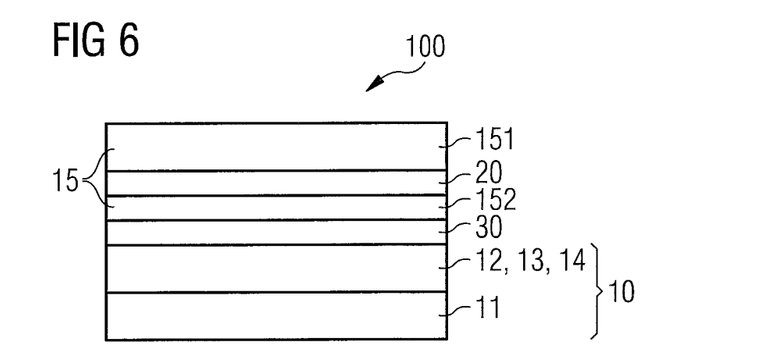

FIG. 6 shows a schematic side view of an organic optoelectronic component 100 according to an example. The organic optoelectronic component 100 has a functional component part 10. A further camouflage layer 30 is arranged downstream of the functional component part 10. An adhesive layer 152, a camouflage layer 20 and a protective layer 151 are arranged downstream of the further camouflage layer 30. The protective layer 151 and the adhesive layer 152 can form the encapsulation 15 or at least a part of the encapsulation 15. The component 100 can thus have two camouflage layers 20, 30 having the function of falsifying the IR or Raman or EDX signal of the used materials. The IR-active and/or Raman-active and/or EDX-active materials can alternatively also be added to the adhesive layer 152. A separate camouflage layer 20, 30 can thus be avoided. In particular, the camouflage layers 20, 30 are arranged outside the beam path of the organic optoelectronic component 100.

The following table shows characteristic groups and framework frequencies of vibration spectroscopy for IR-active materials, for example, materials of the camouflage layer 20 or of the functional component part 10:

| Wave Number [cm$^{-1}$] | Band Form | Vibration-Type | Compound Class |
|---|---|---|---|
| 3600-3200 | b | ν (OH) | Alcohols, phenols |
| 3550-3350 | b | ν (NH) | Amines (primary amine-2 bands) |
| 3200-2400 | m, sb | ν (OH) | Carboxylic acids |
| 3100-3000 | m-w | ν (=C—H) | Aromatics, olefins |
| 3000-2800 | s-m | ν (—C—H) | Saturated hydrocarbons |
| 2960, 2870 | s-m | ν (—CH$_3$) | Saturated hydrocarbons |
| 2925, 2850 | w | ν (—CH$_2$) | Saturated hydrocarbons |
| 2600-2550 | w | ν (—S—H) | Thiols, thiophenols |
| 2300-2100 | m-s | ν (—C≡X) | Acetylenes (X = C), nitriles (X = N) |
| 2270-2000 | s | ν (—X=C=Y) | Isocyanates, isothiocyanates, nitriles |
| 1850-1600 | s | ν (—C=O) | Carbonyl compounds |
| 1675-1630 | m | ν (—C=C) | Olefins |
| 1650-1620 | s | δ (—NH$_2$) | Primary acid amides (amide bands) |
| 1650-1550 | m | δ (—N—H) | Primary and secondary amines |
| 1610-1590 | m | ν (—C=C) | Ring vibration of the aromatics |
| 1560-1515 | s | ν (—NO$_2$) | Nitro compounds |
| 1500-1480 | m | ν (—C=C) | Ring vibration of the aromatics |
| 1470-1400 | s-m | δ (—C—H) | Saturated hydrocarbons |
| 1460-1420 | m | ν (—C=C) | Ring vibration of the aromatics |
| 1420-1330 | s | ν (—SO$_2$) | Sulfonyl compounds |
| 1390-1370 | s | δ (—CH$_3$) | Saturated hydrocarbons |
| 1360-1030 | m-s | δ (C—N) | Amides, amines |
| 1350-1240 | s | ν (NO$_2$) | Nitro compounds |
| 1300-1020 | ss-s | ν (—C—O—C) | Ethers, esters, anhydrides, acetals |
| 1200-1145 | m-s | ν (—SO$_2$) | Sulfonyl compounds |
| 1070-1030 | s | ν (—S=O) | Solfoxides |
| 970-960 | s | δ (=C—H) | Olefins |
| 840-750 | s | δ (=C—H)o.o.p | Substituted benzenes |
| 800-500 | m-w | ν (—C-Hal) | Halogen compounds |
| 800-600 | m-w | ν (—C—S) | Thiols, thioethers |

Figure 7:
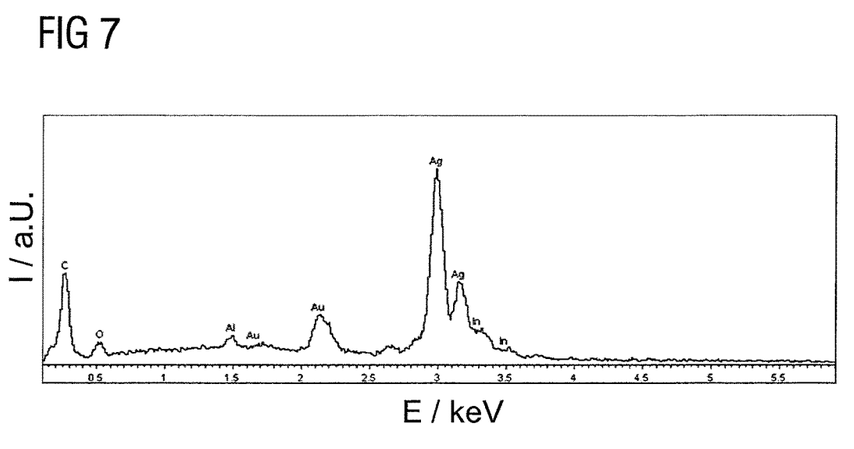
FIG. 7 shows an EDX spectrum according to an example.

Band shape
ss = very strong,
s = strong,
m = means,
w = weak,
b = wide,
sb = very wide FIG. 7 shows an EDX spectrum, that is to say a spectrum recorded by energy-dispersive X-ray spectroscopy, of a conductor track. The intensity I in a.U. (arbitrary units) is shown as a function of the energy E in keV. A strong silver signal (Ag) and a gold interference signal (Au) can be seen from the spectrum. The gold interference signal can be the signal of the camouflage layer. The silver signal can be the signal of the functional component part. Owing to the presence of a camouflage layer in an organic optoelectronic component, identification of the material composition of the functional component part can be made more difficult or prevented.

The examples described in conjunction with the figures and the features thereof can also be combined with one another in accordance with further examples, even if such combinations are not explicitly shown in the figures. Furthermore, the examples described in conjunction with the figures can have additional or alternative features according to the description in the general part.

Our components and methods are not restricted to the examples by the description on the basis of the examples. Rather, this disclosure encompasses any new feature and also any combination of features including in particular any combination of features in the appended claims, even if the feature or combination itself is not explicitly specified in the claims or examples.

This application claims priority of DE 10 2016 103 821.0, the subject matter of which is incorporated herein by reference.

The invention claimed is:

1. A method of preventing an analysis of the material composition of an organic optoelectronic component comprising:
   A) providing an organic optoelectronic component comprising a functional component part and a camouflage layer, and
   B) determining an overall analysis spectrum of the organic optoelectronic component by IR or X-ray radiation,
   wherein the overall analysis spectrum is composed of a first analysis spectrum of the functional component part and a second analysis spectrum of the camouflage layer, and
   determination of the first and/or second analysis spectrum from the overall analysis spectrum is prevented so that, due to the camouflage layer, determination of the material composition of the functional component part is prevented.

2. The method according to claim 1, wherein the first and second analysis spectra are each an IR or Raman spectrum.

3. The method according to claim 1, wherein the first and second analysis spectra are each an EDX spectrum.

4. The method according to claim 1, wherein the camouflage layer is arranged between a second electrode and an encapsulation, and the second electrode is arranged downstream of a first electrode.

5. The method according to claim 1, wherein the camouflage layer is arranged between a substrate and a first electrode.

6. The method according to claim 1, wherein the camouflage layer is arranged outside a beam path of electromagnetic radiation of the functional component part.

7. The method according to claim 1, wherein the camouflage layer has a thickness of 20 nm to 5000 nm.

8. The method according to claim 1, wherein an encapsulation has a layer structure comprising a protective layer and an adhesive layer, and the camouflage layer is arranged between the protective layer and the adhesive layer.

9. The method according to claim 8, further comprising another camouflage layer, wherein the another camouflage layer has a different material composition compared to the camouflage layer, and the another camouflage layer is arranged between the organic functional layer stack and the adhesive layer.

10. The method according to claim 1, wherein an encapsulation has a layer structure comprising a protective layer and an adhesive layer, the adhesive layer forms the camouflage layer, and the adhesive layer has IR-active materials that impedes or prevents an analysis of the material composition of the functional component part.

11. The method according to claim 1, wherein the camouflage layer contains materials not present in the functional component part.

12. The method according to claim 1, wherein the camouflage layer contains an inorganic material or an oxide of the inorganic material selected from the group consisting of Si, In, Al, Ag, Cu, Pt, Ti, Ir, Sn and Zn.

13. The method according to claim 1, wherein the camouflage layer contains an organic polymeric material selected from the group consisting of polyimide, poly (p-phenylene), poly (p-phenylene-vinylene), acrylate, epoxide, silicone and polyurethane.

14. The method according to claim 1, wherein the camouflage layer is arranged at a side of the organic functional layer stack facing away from an emission surface.

15. The method according to claim 1, wherein the camouflage layer contains an inorganic material or an oxide of the inorganic material selected from the group consisting of In, Al, Ag, Cu, Pt, Ti, Ir, Sn and Zn.

16. An organic optoelectronic component, comprising a functional component part and a camouflage layer, wherein the functional component part comprises
 a substrate,
 a first electrode on the substrate,
 an organic functional layer stack on the first electrode,
 a second electrode arranged at least in regions on the organic functional layer stack, and
 an encapsulation on the second electrode,
 wherein the functional component part emits electromagnetic radiation and has a first analysis spectrum,
 the camouflage layer has a second analysis spectrum,
 the first analysis spectrum and the second analysis spectrum are different from one another, overlap at least in some regions, and form an overall analysis spectrum of the organic optoelectronic component such that, due to the camouflage layer, an analysis of the material composition of the functional component part is prevented.

17. The method according to claim 16, wherein the encapsulation comprises a plurality of layers.

* * * * *